(12) United States Patent  
Thibodo, Jr.

(10) Patent No.: US 6,561,995 B1  
(45) Date of Patent: May 13, 2003

(54) SPLINT SYSTEM FOR TWO OR MORE ADJACENT FINGERS OF THE HAND

(76) Inventor: Calvin Thibodo, Jr., 1061 Grandview Blvd., Kansas City, KS (US) 66102

( * ) Notice: Subject to any disclaimer, the term of this patent is extended or adjusted under 35 U.S.C. 154(b) by 117 days.

(21) Appl. No.: 09/655,904

(22) Filed: Sep. 6, 2000

(51) Int. Cl.[7] .................................................. A61F 5/00
(52) U.S. Cl. ........................... 602/22; 602/21; 128/880
(58) Field of Search .................................. 602/5, 20–22, 602/60–61, 64; 128/878–880; 482/44, 49; 2/161.1, 163

(56) References Cited

U.S. PATENT DOCUMENTS

| | | | |
|---|---|---|---|
| 1,220,476 A | * 3/1917 | Ujdur | ........................... 602/21 |
| 3,756,222 A | * 9/1973 | Ketchum | ..................... 482/44 |
| 4,103,682 A | 8/1978 | Franzl | |
| 4,765,320 A | 8/1988 | Lindemann et al. | |
| 4,781,178 A | 11/1988 | Gordon | |
| 4,862,877 A | 9/1989 | Barber | |
| 4,960,114 A | * 10/1990 | Dale | ........................... 602/21 |
| 5,027,802 A | 7/1991 | Donohue | |
| 5,267,945 A | 12/1993 | Doctor et al. | |
| 5,328,448 A | * 7/1994 | Gray, Sr. | ..................... 602/22 |
| 5,333,605 A | 8/1994 | Matsumura et al. | |
| D387,826 S | * 12/1997 | Smallwood | ................ D21/198 |
| 5,725,490 A | 3/1998 | Conran | |
| 5,746,707 A | * 5/1998 | Eck | |
| 5,947,915 A | 9/1999 | Thibodo, Jr. | |
| 6,182,293 B1 | * 2/2001 | Mustin | ........................ 2/161.1 |

* cited by examiner

Primary Examiner—Denise M. Pothier  
(74) Attorney, Agent, or Firm—Kenneth W. Iles

(57) ABSTRACT

A splint system for two or more adjacent fingers of the hand includes a splint body for with the splint member for any particular finger having an extension member with a depending tongue that is received in a receiving channel formed in the end of the splint body portion of the splint for a particular finger. The fingers may be splinted along a straight line or with one or more phalanges bent at an angle to the general normal axis of a finger.

9 Claims, 11 Drawing Sheets

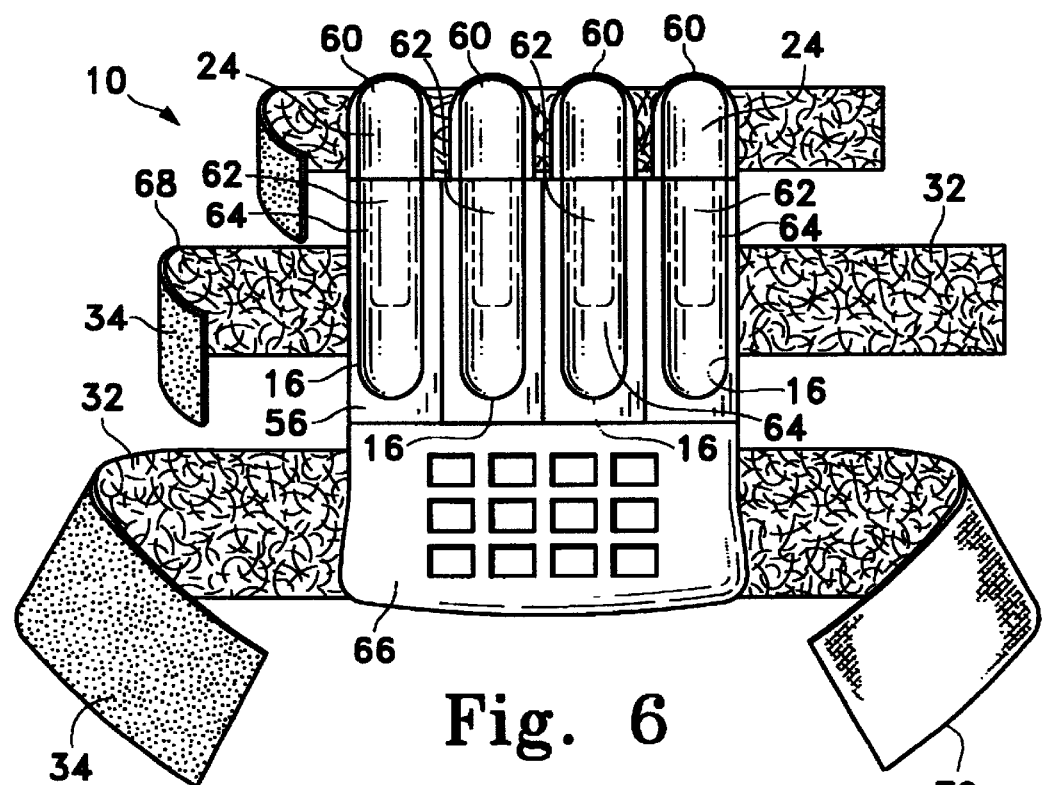
Fig. 6
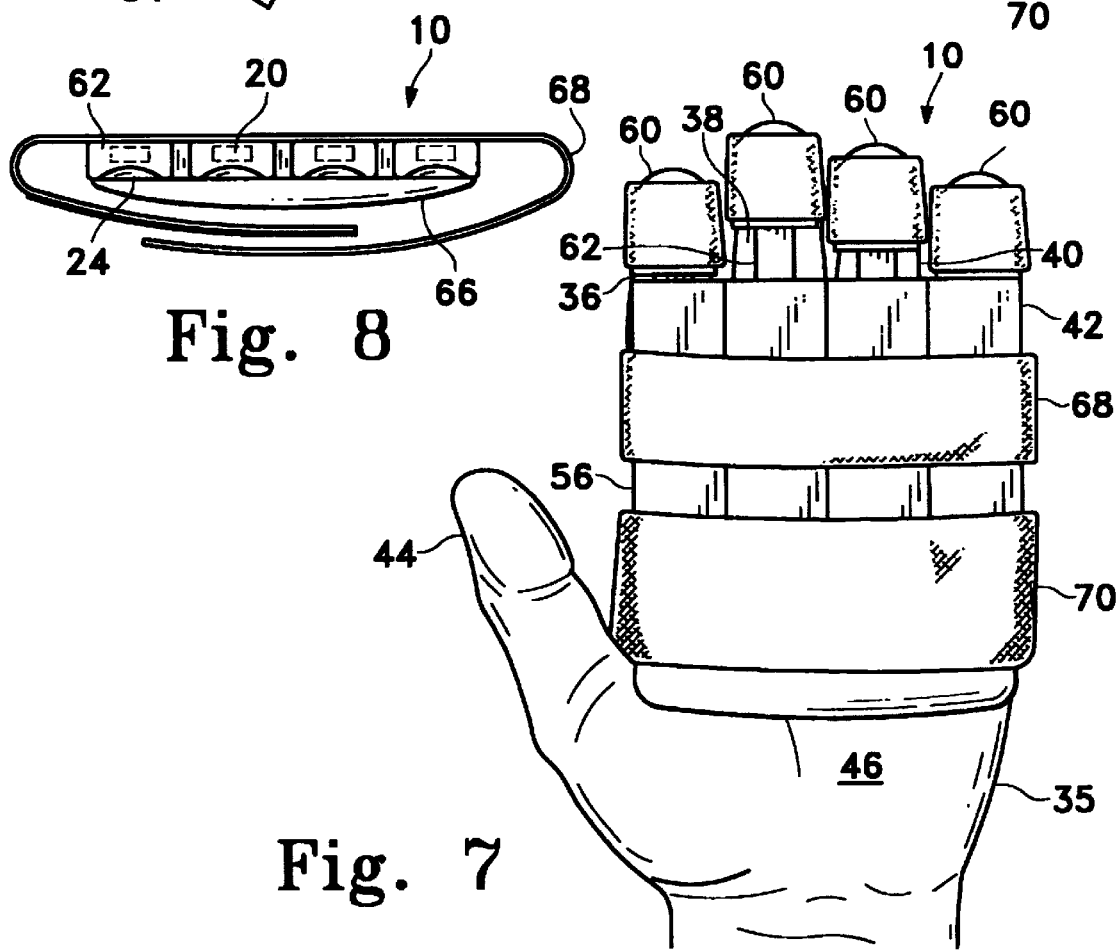
Fig. 8
Fig. 7

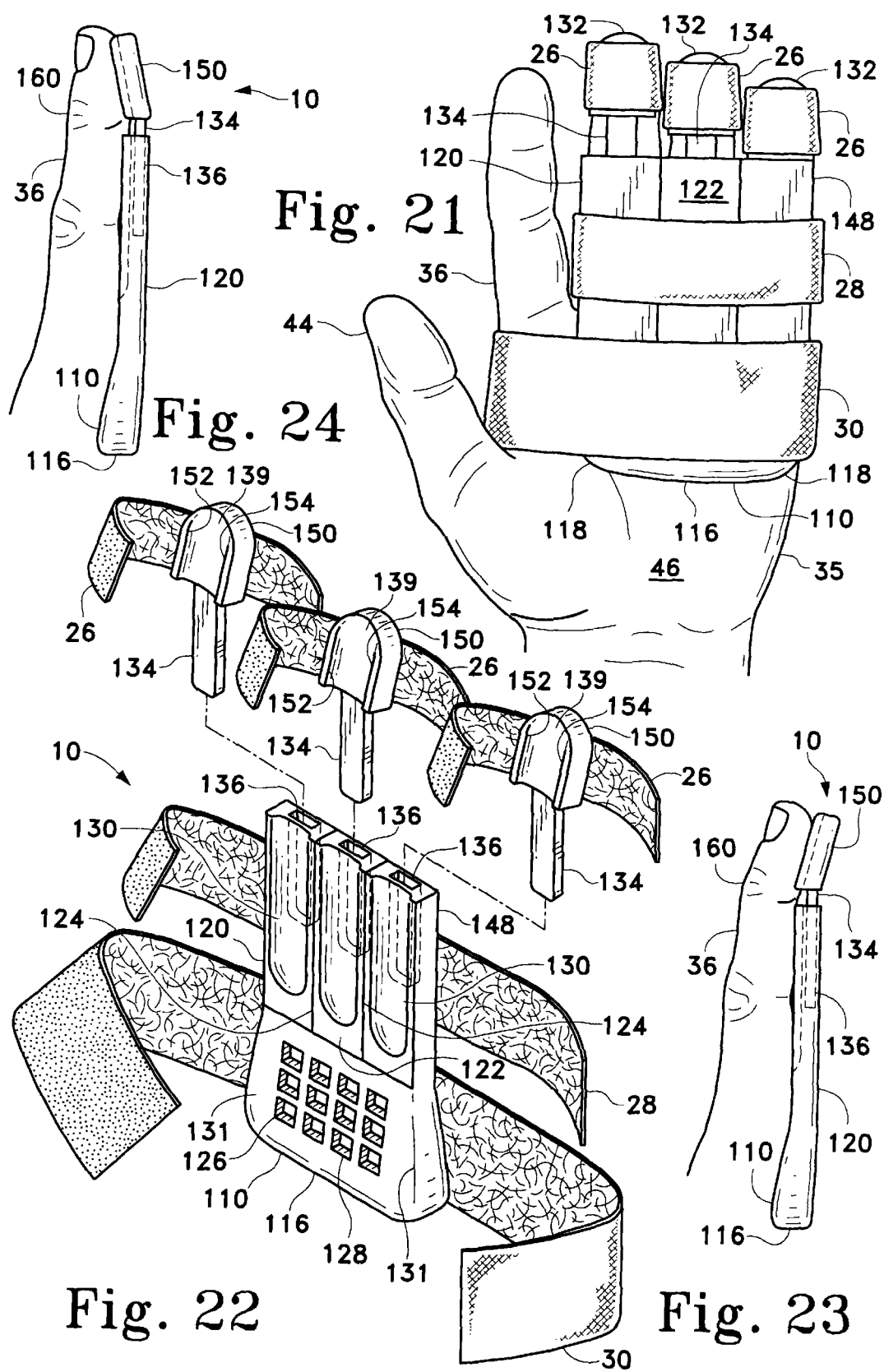

SPLINT SYSTEM FOR TWO OR MORE ADJACENT FINGERS OF THE HAND

CROSS REFERENCE TO RELATED APPLICATIONS

Not Applicable.

STATEMENT REGARDING FEDERALLY SPONSORED RESEARCH OR DEVELOPMENT.

Not Applicable

BACKGROUND OF THE INVENTION

1. Field of the Invention.

The present invention is related to an apparatus for splinting fingers. More particularly, the present invention is directed to a splinting system that is easily adaptable for fingers of different lengths.

2. Description of Related Art Including Information Disclosed Under 37 C.F.R. Sections 1.97–1.99.

Injuries to fingers and hands are common and typical causes include trauma causing broken bones, strained ligaments and tendons and the like, carpal tunnel syndrome, repetitive motion injury, and the like. Frequently treatment requires that the affected finger or fingers be immobilized with a splint.

Prior art splints are typically either very simple or very complex. Simple splints include, for example, straight flat wooden or metal sticks that are bound to the affected fingers. Such splints do not allow a finger to be bent in any particular manner, merely holding the finger straight. In some cases proper healing requires that the affected finger or fingers be bent at one or more knuckles, either upwardly or downwardly, which cannot be readily accomplished with a straight splint. Moreover, such splints do not conform with the basically cylindrical shape of the fingers and are therefore not comfortable and cannot be securely attached to the finger or fingers.

Other simple splints are formed from bent metal, such as aluminum, and may include an elongated trough shape designed to fit more closely to the finger and may include a curved upper end designed to protect a finger tip. Foam padding may be attached to the inner surface of such a splint. This type of splint, however, also holds the finger in a straight position.

More complex splints are very complicated and have many parts, such as Lindemann et al. U.S. Pat. No. 4,756,230, Gordon U.S. Pat. No. 4,781,178 and Donohue U.S. Pat. No. 5,027,802. Lindemann '320, for example, includes a collar applied over each finger and are connected to a forearm band by an elastic band. Gordon '178 discloses an orthopedic glove with one or more splints affixed at selective locations to immobilize and join and/or the wrist of the hand and is designed to immobilize particular joints having arthritis. Donohue '802 discloses a traction system for fingers that includes a traction element under the fingers or hand. All of these devices are complex, expensive and adapted to highly specific and relatively unusual finger problems. They are not suitable for more typical strains and broken bones.

The splints discussed above do not easily allow the separate or combined splinting treatment of any desired number of fingers at one time with a single device. Nor do these devices embody a splint of adjustable length splints that therefore can be used with fingers of different lengths on either different patients or on different fingers of the same patient's hand.

Therefore, there is a need for a finger splint system that easily allows the or combined splinting treatment of two or more adjacent fingers at one time with a single device; that can be used with fingers of different lengths on either different patients or on different fingers of the same patient's hand; that can be used for two or three fingers; that allows fingers to be splinted into the optimal position for healing; and that is easy to use.

BRIEF SUMMARY OF THE INVENTION

Accordingly, it is a primary object of the present invention to provide a finger splint system for two or more adjacent finger that easily allows the separate or combined splinting treatment of any desired number of fingers at one time with a single device;

It is another object of the present invention to provide a finger splint system for two or more adjacent fingers that can be used with fingers of different lengths on either different patients or on different fingers of the same patient's hand.

It is another object of the present invention to provide a finger splint system for two or more adjacent fingers that can be used for two or more fingers.

It is another object of the present invention to provide a finger splint system for two or more adjacent fingers that allows fingers to be splinted into the optimal position for healing.

It is another object of the present invention to provide a finger splint system for two or more adjacent fingers that is easy to use.

These objects are achieved by providing an elongated basically rectangularly shaped solid splint having a concave inner surface curved to fit over the essentially cylindrical shape of the finger, with a somewhat bulbous base at the bottom for fitting comfortably into the palm of the patient. An extension member at the tip includes an elongated tongue that fits into a matching slot in the top of the splint body.

In another embodiment, the upper tip of the splint is bent to require the upper phalange of the splinted finger to be bent either downwardly or upwardly of its normal position, as required by the medical condition being treated.

In another embodiment, four such splints are ganged together into a single unit for splinting four fingers. The individual splint members are frangible and can easily be removed from the body of the splint device if there is not need of any particular single splint in a particular application.

In another embodiment, the thumb finger in particular is splinted with a splint system having a relatively large palm pad and a straight angled member for supporting the thumb.

In another embodiment, the fingers are loosely splinted and restrained from curling excessively into the palm, which, particularly in older patients, can exacerbate a tendency for the tendons to shorten, resulting in permanent cramping of the fingers. This embodiment comprises a solid rounded block fitted into the palm with four grooves along an upper edge for seating and restraining the bases of the four fingers, excluding the thumb finger.

In all embodiments, the splint or splint system is held on the finger or hand by a series of straps, preferably three straps, that wrap around the hand and affected finger or fingers and are fastened to themselves. In the preferred embodiments, the straps are fastened to themselves with hook and loop type fasteners.

The splint system for one or more digits of the hand disclosed herein is conveniently made in three basic sizes, which are small, medium, and large, to accommodate different hands of substantially different sizes. The splint system is also provided with models that splint any two or any three fingers, as well as an embodiment for the four parallel fingers. That is, the index and middle finger; the middle and ring finger; and the ring finger and pinkie finger, as well as, for example the index finger and ring finger and other combinations can be splinted with a single device. This principle is also used to provide a splint for any combination of three parallel fingers, whether or not they are all adjacent to one another.

In this specification, the term digit may be used interchangeably with the terms finger or thumb.

Other objects and advantages of the present invention will become apparent from the following description taken in connection with the accompanying drawings, wherein is set forth by way of illustration and example, the preferred embodiment of the present invention and the best mode currently known to the inventor for carrying out his invention.

BRIEF DESCRIPTION OF THE SEVERAL VIEWS OF THE DRAWING

FIG. 6 is a rear elevation of an alternative embodiment of the finger splint of FIG. 1 for use in splinting four or fewer fingers on one hand.

FIG. 7 is a front elevation of the splint of FIG. 6.

FIG. 8 is a top plan view of the splint of FIG. 6.

FIG. 21 is a right front perspective view of a the splint of FIG. 18 showing the use of bent tip extension members.

FIG. 22 is a side elevation of the splint of FIG. 14 or 18 showing bent tip extension members bending the distal tip of the fingers forward.

FIG. 23 is a side elevation of the splint of FIG. 14 or 18 showing bent tip extension members bending the distal tip of the fingers backward.

FIG. 24 is a perspective view of an embodiment of the bent tip extension member of FIG. 21 adapted for use when bent forward or backward.

DETAILED DESCRIPTION OF THE INVENTION

As required by the Patent Statutes and the case law, the preferred embodiment of the present invention and the best mode currently known to the inventor for carrying out the invention are disclosed in detail herein. The embodiments disclosed herein, however, are merely illustrative of the invention, which may be embodied in various forms. Therefore, specific structural and functional details disclosed herein are not to be interpreted as limiting, but merely to provide the proper basis for the claims and as a representative basis for teaching one skilled in the art to which the invention pertains to make and use the apparatus disclosed herein as embodied in any appropriately specific and detailed structure.

Figure 1:
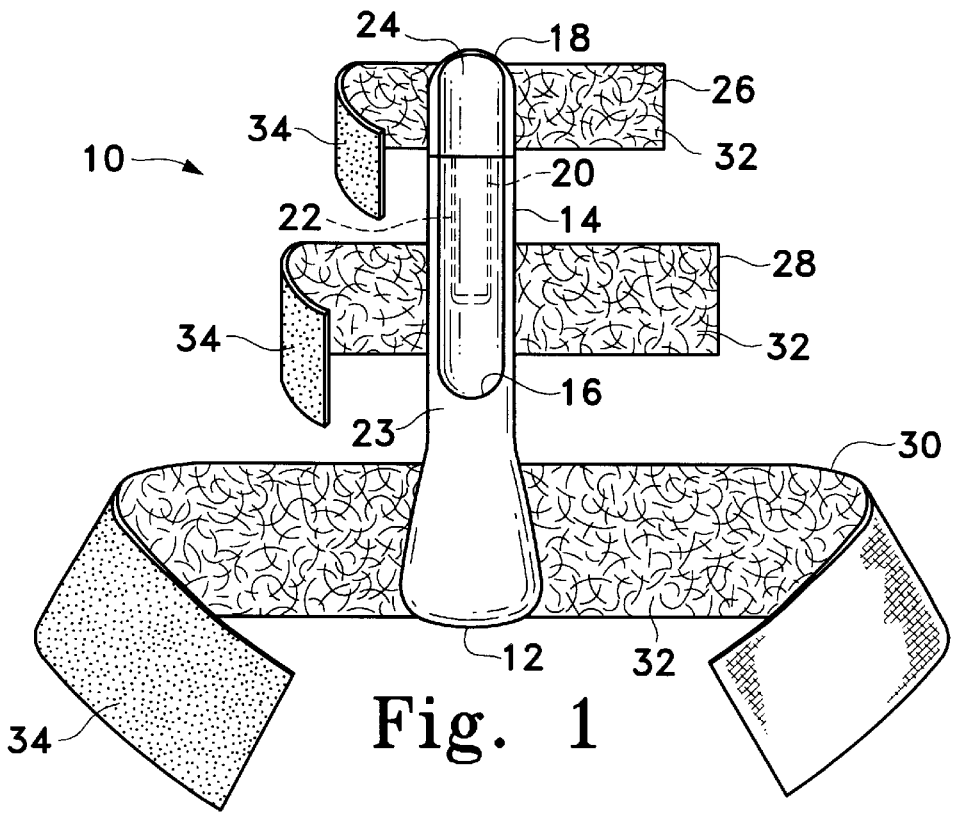
FIG. 1 is rear elevation of an adjustable finger splint according to the present invention for any single finger.
Figure 2:
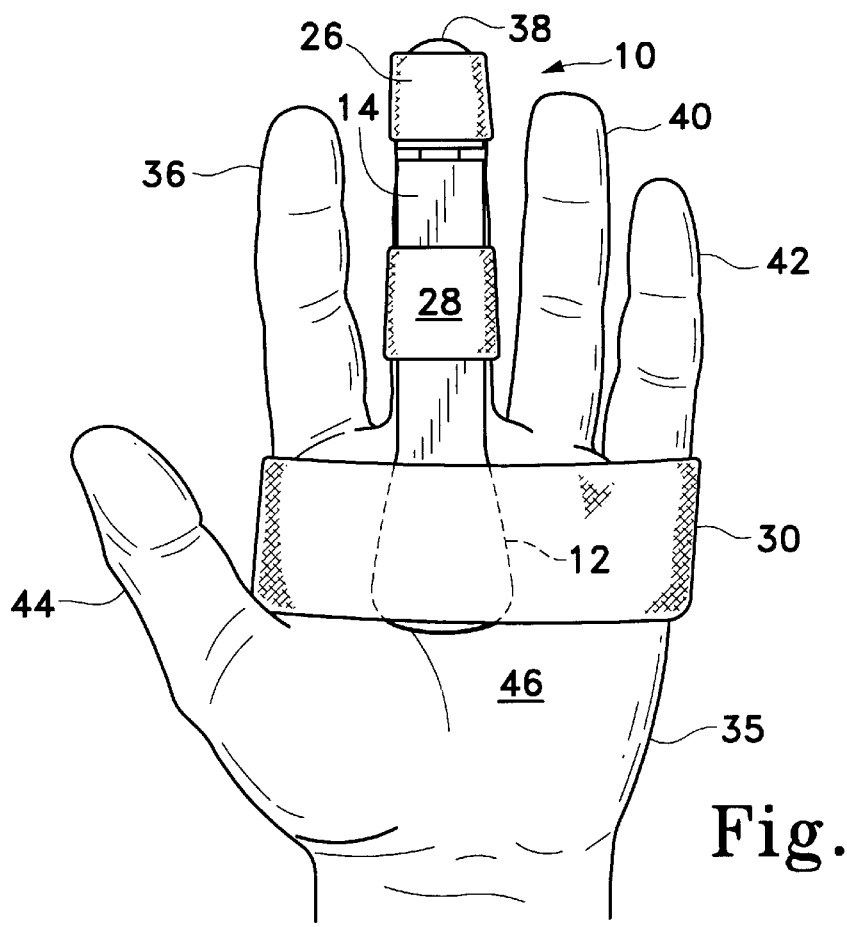
FIG. 2 is a front elevation of the finger splint of FIG. 1 shown installed on the middle finger of a hand (palm side toward viewer).
Figures 3, 4, 5:
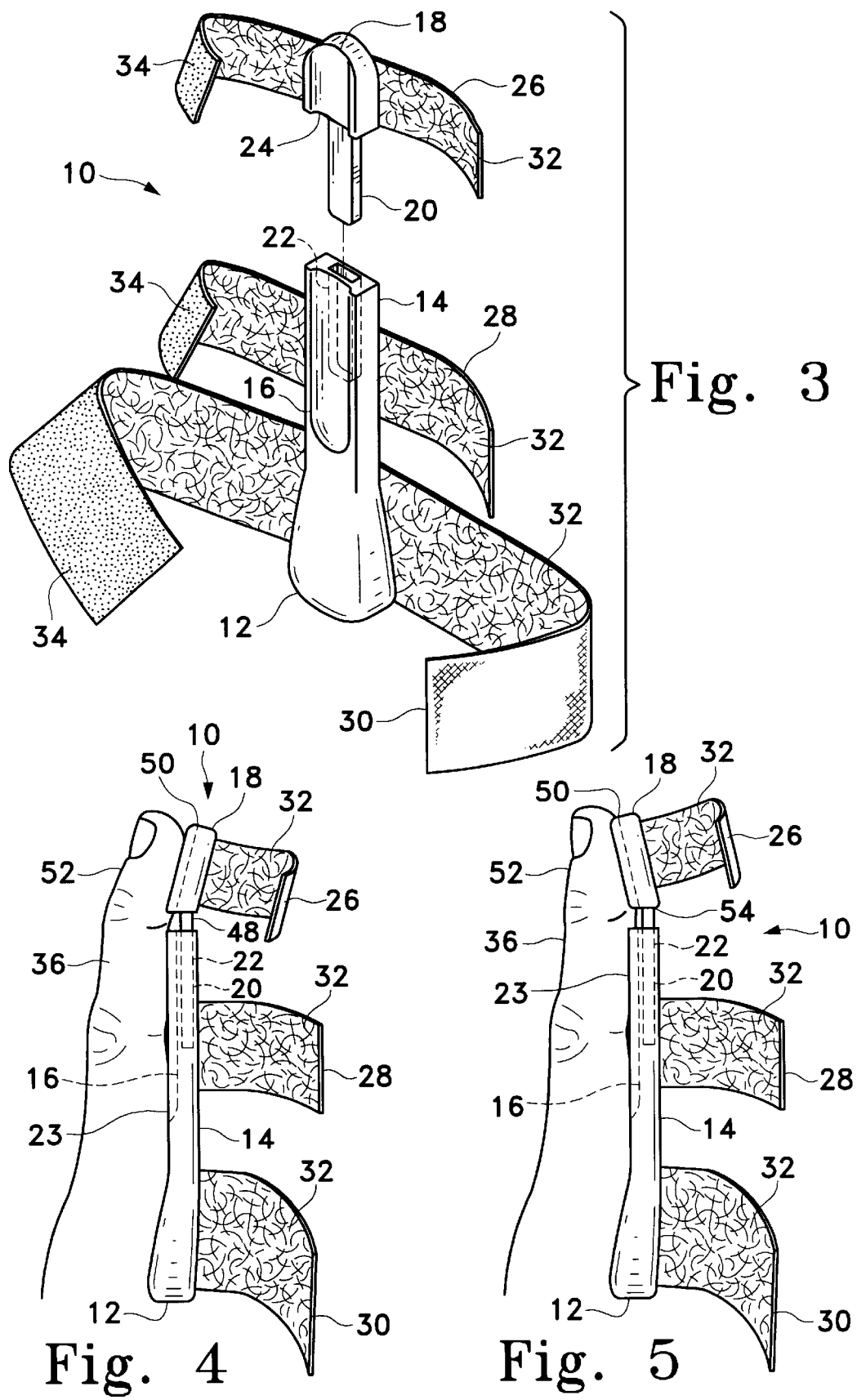
FIG. 3 is a right-hand front perspective view of the splint of FIG. 1, illustrating the extension member of the splint and the concave channel curvature of the splint for closely matching the cylindrical shape of a digit.
FIG. 4 is a side elevation of an alternative embodiment of the splint of FIG. 1 having a tip bent to hold the upper flange of the digit in a downward position toward the palm and shown applied to a digit.
FIG. 5 is a side elevation of the alternative embodiment of FIG. 1 having a tip bent upward relative to the normal straight line of the finger, that is, as opposed to the direction that the knuckle normally bends.

Referring now to FIGS. 1 and 3, there is shown a splint system for one or more digits of the hand 10, or splint system 10, for one finger having a bulbous base 12 and a splint member body 14 consisting of a single member. A splint member is that portion of the splint system 10 that will split or support one digit, and each splint member also includes a splint body. The elongated splint member body 14 includes an elongated channel recess 16, which is roughly a portion of a cylinder, for receiving and conforming to the basically cylindrical shape of a finger, thereby providing more support than a flat surface would, as the elongated channel recess 16 cradles the finger. The elongated channel recess 16 faces toward the view in FIG. 1 and is against the finger in FIG. 2. An extension member tip 18 includes a depending tongue member 20 that is received for reciprocal movement in an extension member tongue receiving channel 22 in the splint member body 14. By sliding the extension member tongue up or down within the receiving channel 22, a medical care worker or a patient can adjust the length of the overall splint member 23 to fit different lengths of fingers. The fit between the extension tongue member 20 and the extension member tongue receiving channel 22 is firm enough to allow easy adjustment but to retain a desired length adjustment through frictional engagement of the parts. The extension tip member includes an extension member channel recess 24 that aligns with and continues the channel recess 16 in the splint member body 14.

Figure 9:
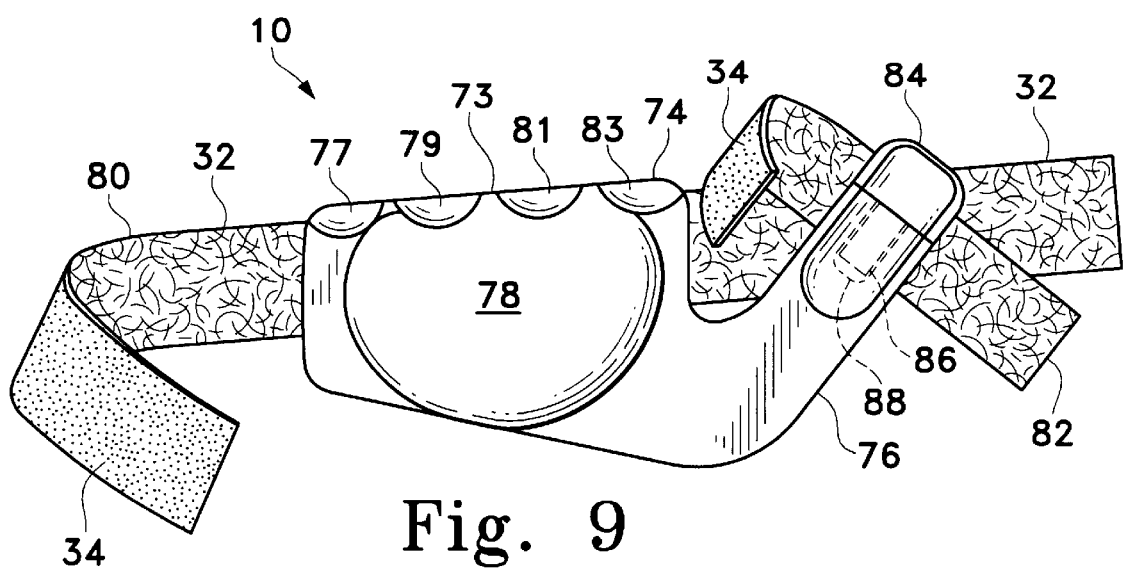
FIG. 9 is rear elevation of a digit splint according to the present invention specially adapted for use on the thumb digit.
Figure 10:
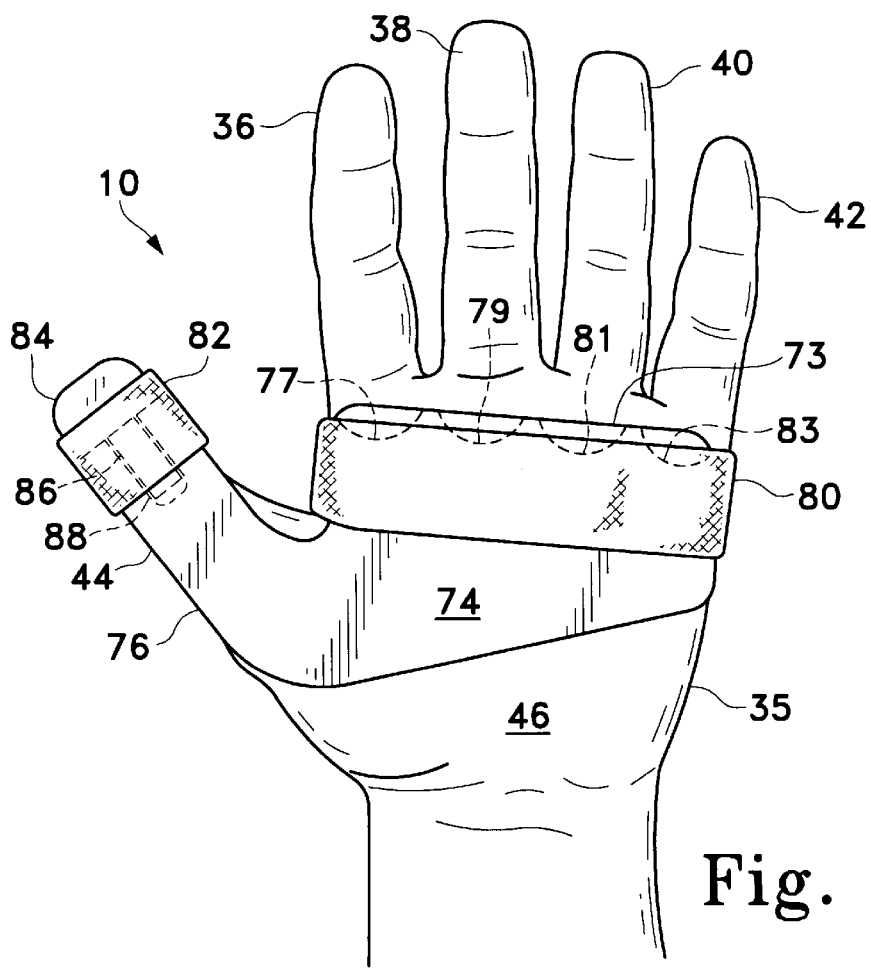
FIG. 10 is a front elevation of the thumb splint of FIG. 9 shown attached to a left hand.

Referring to FIGS. 1, 2, and 3, the splint system 10 also includes a plurality of fastening straps for securing the splint system 10 to the finger and hand. Although a left hand is illustrated in FIGS. 2, 7, 10, and 12, the embodiments of the invention illustrated in FIGS. 1–8 may be used on either hand without modification, while the embodiment illustrated in FIGS. 9 and 10 is provided in left-handed and right-handed models, which are merely mirror images of each other. A short hook and loop fastener strip 28 located toward the upper end of the splint system wraps around the upper end of the finger, such as the middle finger 38 in FIG. 2; a long hook and loop fastener strip 30 wraps around the hand 35 across the palm 46; and an intermediate length hook and loop fastener strip 28 wraps around the first phalange of the middle finger 38. Each of the hook and loop fasteners trips 26, 28, and 30 includes a hook portion 32 and a loop portion 34 so that each strip can be fastened to itself and the tension on each strip can be adjusted to a comfortable firmness that fully supports the splinted digit. The fastener strips 26, 28, and 30 are attached to the overall splint member 23 by an adhesive, with the fastener strips 28, 30 being fastened to the splint member body 14 and the fastener strip 26 being fastened to the extension tip member 18. Alternatively, the fastener strips 26, 28, and 30 may be held in place only by frictional engagement with the treated digit without being permanently fastened to the splint system 10.

Referring now to FIGS. 4 and 5, the splint system in an alternative embodiment is constructed as described above with one change, which is that the installed extension member tip 18 is bent away from the straight line axis of the splint member body 14. In FIG. 4, the splint system 14 further includes an inward bend 48 at the juncture of the finger retaining portion 50 of the extension tip member 18 and the extension member tongue 20, so that the third phalange 52 of the finger 36 is bent forward toward the palm when the splint system 10 is fastened to the finger 36, which is illustrated as the index finger, although this splint system 10 could be used on any digit. In FIG. 5, an outward bent 54 is formed at the juncture of the finger retaining portion 50 of the extension tip member 18 and the extension member tongue 20, so that the third phalange 52 of the finger 36 is bent rearward away from the palm and toward the back of the hand when the splint system 10 is fastened to the finger 36, which is illustrated as the index finger, although this splint system 10 could be used on any digit. In a variety of injury and health situations, it is sometimes necessary to bend the third phalange 52 of one or more fingers either outward or inward during the healing process in order to insure that the healed finger will be straight. The embodiments of the splint system illustrated in FIGS. 4 and 5 are designed to achieve the healing of a damaged finger into a final straight position.

Referring now to FIGS. 6, 7, and 8, an alternative splint system 10 has been adapted for splinting of the four principal fingers of either hand. A basically U-shaped splint body 56 includes four finger receiving channels 16 like those described above, and four extension tip member 60, each having an extension member tongue 62 that is received in a respective extension member tongue receiving channel 64 in the upper end of the splint body 56. A bulbous base portion 66 of the splint body 56 fills the hollow of the palm 46, allowing the fingers 36, 38, 40, and 42 to be splinted straight relative to the general orientation of the hand. Finger 36 is the index finger, finger 38 is the middle finger, finger 40 is the ring finger, finger 42 is the pinkie finger, and finger 44 is the thumb. The hook and loop fastener strap 68 fastens the splint system 10 to the fingers 36, 38, 40, and 42 together and the hook and loop fastener strap 70 fastens the splint system 10 to palm 46 by passing about the palm 46 and the back of the hand. The fastener straps 68 and 70 operate as described above. The use of the extension tip members 60, their seating in the extension member tongue receiving channels 64 and their adjustment are as described above. This allows a splint body having a substantially straight line top edge and one basic size to be used with different hands of substantially different sizes. As shown in FIG. 6, for example, the upper tips of the extension members 60 form a straight horizontal line, but when installed on a hand, as shown in FIG. 7, the lengths of each finger supporting portion of the splint system 10 are different as the amount of extension is adjusted to match the length of each finger. The splint body 56 includes four elongated parallel channel recesses 16, and each extension tip member 60 also includes an extension member channel recess 24 for receiving and cradling each of the four splinted fingers, as described above relative to FIGS. 1, 2 and 3. In FIG. 7, these channels 16, 24 are not seen because they are against the palm side of the left hand 35.

Still referring to FIGS. 6–8, each splint member is adapted to extend only from the metacarpals to the proximal phalange of the user's fingers, which each said splint member covers, with the remaining portion of the fingers being covered by the adjustable extension tip members 60.

Referring now to FIGS. 9 and 10, a splint system 10 specially adapted for splinting the thumb digit 44 includes a trapezoidal shaped base portion 74 having a thumb retaining extension portion 76, which lies at an angle in the range of 40–60 degrees measured in a clockwise direction from a horizontal line through the lowest point of the extension portion 76, with the preferred angle being 50 degrees. This orientation allows the thumb digit to be splinted at a natural angle to the hand. The trapezoidal shaped base portion 74 has protruding basically circular palm pad 78 that fills the hollow of the palm 46 of the left hand 35, allowing the trapezoidal shaped base portion 74 to lie basically flat across the palm side of the left hand 35, while remaining comfortable for the user and keeping the base portion of the hand flat. A palm encompassing strap 80 and a thumb encompassing strap 82 secure the splint system 10 to the hand 35 and thumb 44 in the manner described above. An extension tip member 84 includes an extension member tongue 86 that fits snugly into an extension member tongue receiving slot 88 for length adjustment as described above. The embodiment of the splint system 10 shown in FIGS. 9 and 10 enables the thumb 44 to be splinted into a position basically flat and aligned with the plane of the palm 46, and at a natural angle lying in the range of about 40–70 degrees relative to a horizontal line drawn through the lower base of the palm portion of the hand, with the preferred angle in most cases being 45 degrees. To provide a thumb splint system 10 for the right hand, the front of the splint system 10 (which faces the view as shown in FIG. 9), becomes the rear (shown in FIG. 10) and the basically circular palm pad 78 is placed on the obverse surface of the trapezoidal base portion 74.

Figure 11:
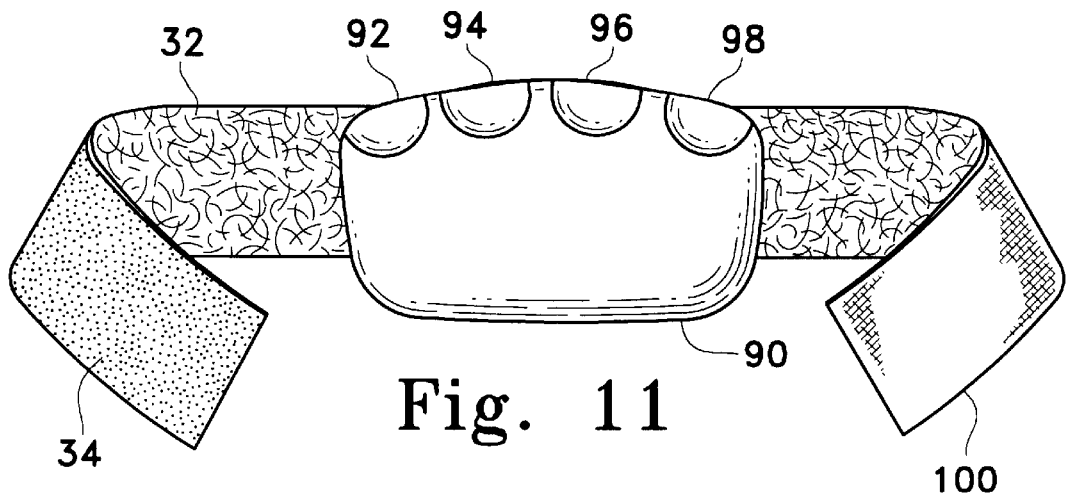
FIG. 11 is a front elevation of the finger restraining splint system according to the present invention.
Figure 12:
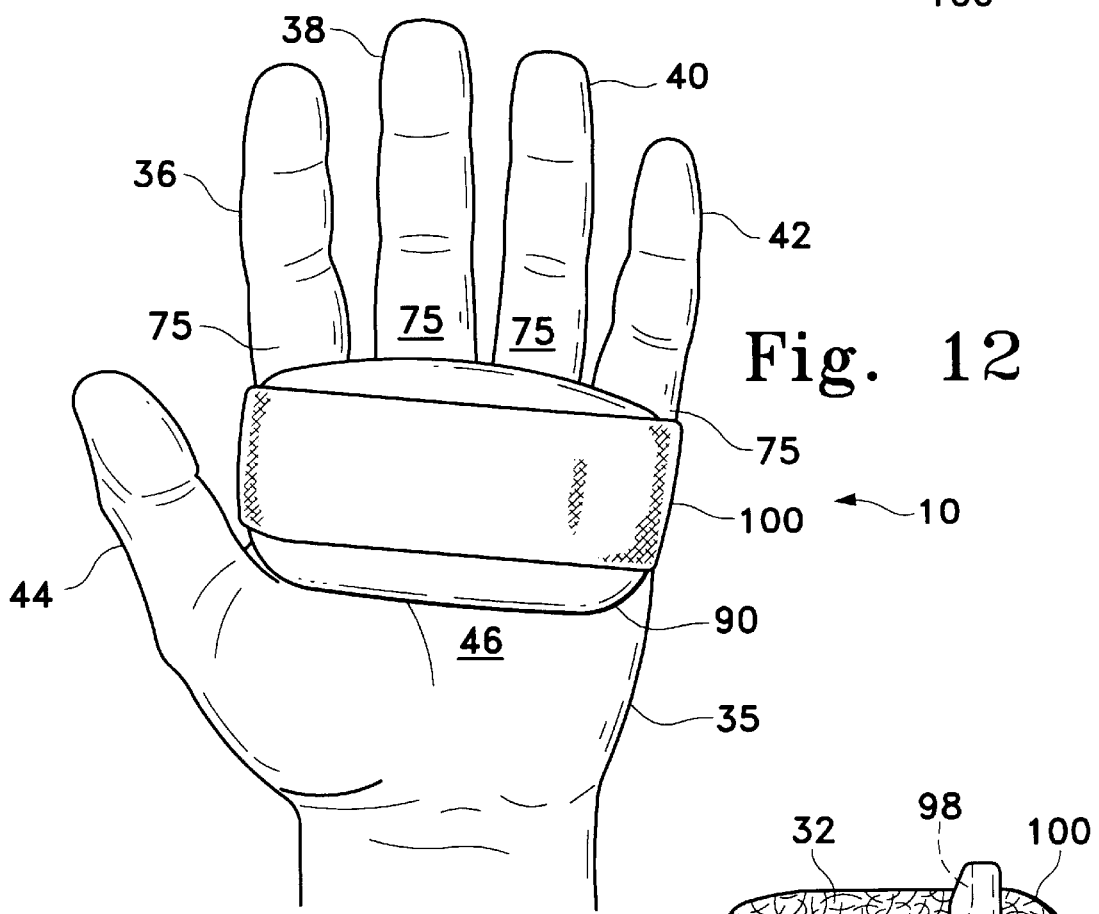
FIG. 12 is a front elevation of the splint system of FIG. 11 shown in use on a left hand.
Figure 13:
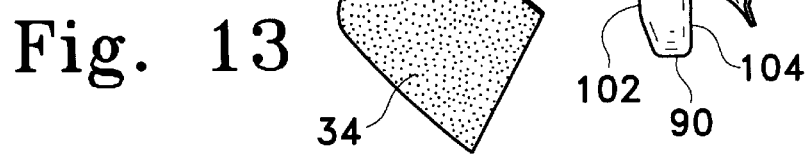
FIG. 13 is a right-hand side elevation of the splint system of FIG. 11.

Referring now to FIGS. 11–13, it is sometimes necessary or desirable to provide support for the bases 75 of the fingers 26, 38, 40 and 42, particularly in the elderly, to prevent the fingers from permanently curling into the palm 46. The embodiment shown in to FIGS. 11–13 is specially adapted for this purpose. The splint system 10 includes a base 90 shaped to conform to the shape of the palm 46 and include indentations for receiving the bases of the fingers 75 (FIG. 12), with indentations to support the bases of the fingers. The indentations 92, 94, 96 and 98 are basically semi-cylindrical in shape and are angled to align with the natural directional orientation of the fingers of normally arranged fingers. The indentation 98, which receives the index finger 36, has a central longitudinal axis that lies at an angle in the range of 65–75 degrees, with the preferred angle being 70 degrees. The indentation 96, which receives the middle finger 38, has a central longitudinal axis that lies at an angle in the range of 85–95 degrees, with the preferred angle being 90 degrees. The indentation 94, which receives the ring finger 40, has a central longitudinal axis that lies at an angle in the range of 105–110 degrees, with the preferred angle being 100 degrees. The indentation 92, which receives the pinkie finger 42, has a central longitudinal axis that lies in the range of 120–130 degree, with the preferred angle being 125 degrees. All angles at measured along a counterclockwise path from a horizontal line through the base of each indentation 92, 94, 96, and 98.

A strap 100, which includes hook portions 32 and loop portions 34 of a hook and loop fastener system, is wrapped about the splint system 10 to secure it to the hand 35. A convex palm facing surface 102 provides fills the hollow of the palm 46, while the obverse side made by flat. The strap 100 may be permanently fastened to the flat side 104 of the base 90.

Figure 14:
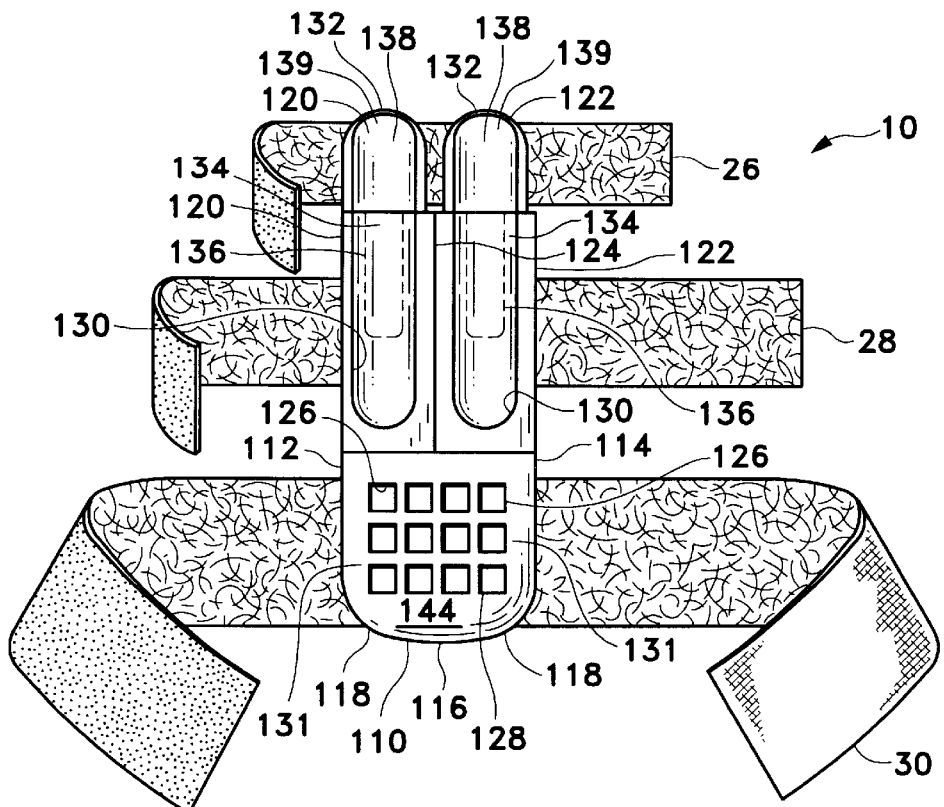
FIG. 14 is a rear elevation of an embodiment of the splint of FIG. 1 for use with any two adjacent fingers.
Figure 15:
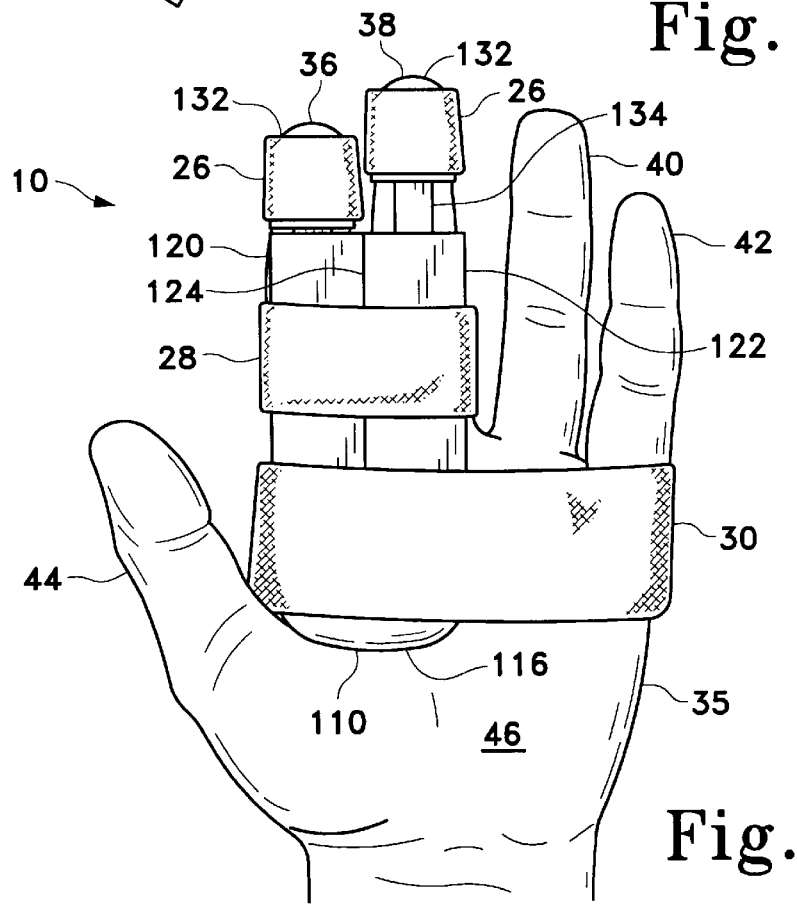
FIG. 15 is a front elevation of the splint of FIG. 14 shown in use on the index and middle fingers of a patient.

Referring now to FIG. 14, there is shown an alternative embodiment of the splint system for two or more adjacent fingers of the hand, or finger splint system 10, which includes a bulbous base 110 having two parallel upstanding side edges, left -hand edge 112 and right-hand edge 114 and a bottom edge 116 connected to each of the side edges by an arcuate corner 118, providing a base bulbous adapted to fit into the palm 46 (See, for example, FIG. 15) directly below the fingers to be splinted. The rear face 144 of the base 12 is shown facing the viewer in FIG. 14 and when the splint system 10 is attached to the left hand 35, the rear face 144 is placed against the palm 46 of the left hand 35. Extending upwardly from the base 10 is a left-hand side splint body member 120 and a left-hand side splint body member 122, which are conjoined along the horizontal seam 124. The base includes an array of twelve cooling cells 126 arranged in a block of four cooling cells 126 by three cooling cells 126 to form a square pattern 128 with a substantial margin 131 between the edges 112, 114, 116 of the bulbous base 110 and the square pattern 128, allowing for cooling of an injection molded plastic splint system 10 without warping. The cooling cells 126 penetrate a portion of the base 110 for a distance sufficient to leave a font wall or face 146 having approximately the same thickness as the width of the margins 131. Each splint body member 120, 122 includes a longitudinal concave groove 130 to accept, receive and cradle the finger being splinted. As shown in FIG. 15, the fingers splinted by the FIG. 14 splint system 10 are the index finger 36 and the middle finger 38 of the left hand 35. The same two-finger splint system 10 can be used on the right hand. Three fastening straps are attached to the splint system 10, a short top strip 26, a middle medium length strip 28, and a lower longest strip 30 for firmly attaching the splint system 10 to the hand as shown in FIG. 15, for example. A separate strip 26 is attached to each of the right-hand and left-hand splint body members 120, 122. The strips or straps 26, 28, and 30 are constructed and operate in the same fashion as strips 26, 28, and 30 in FIG. 1, as described above in relation to FIG. 1. Still referring to FIG. 14, each of the left-hand and right-hand splint body members 120, 122 includes an extension tip member 132 having a connected depending extension member tongue 134 that is slidably inserted into a vertical extension member tongue receiving channel 136, allowing for independent adjustment of the length of the each splint members 120, 122. The extension tip member 132 is held at the desired length by frictional engagement of between the tongue 134 and the receiving channel 136. The extension tip members 132, which are straight as shown in FIGS. 14, 15, further include a longitudinal concave inner surface or tip member finger groove 138 on the fingertip pad 139 that aligns with the grooves 130 to embrace the splinted fingers. The depth of the base 110 and splints 120, 122 is sufficient to provide the required strength of material to accomplish splinting and this is the case in each embodiment.

Figure 16:
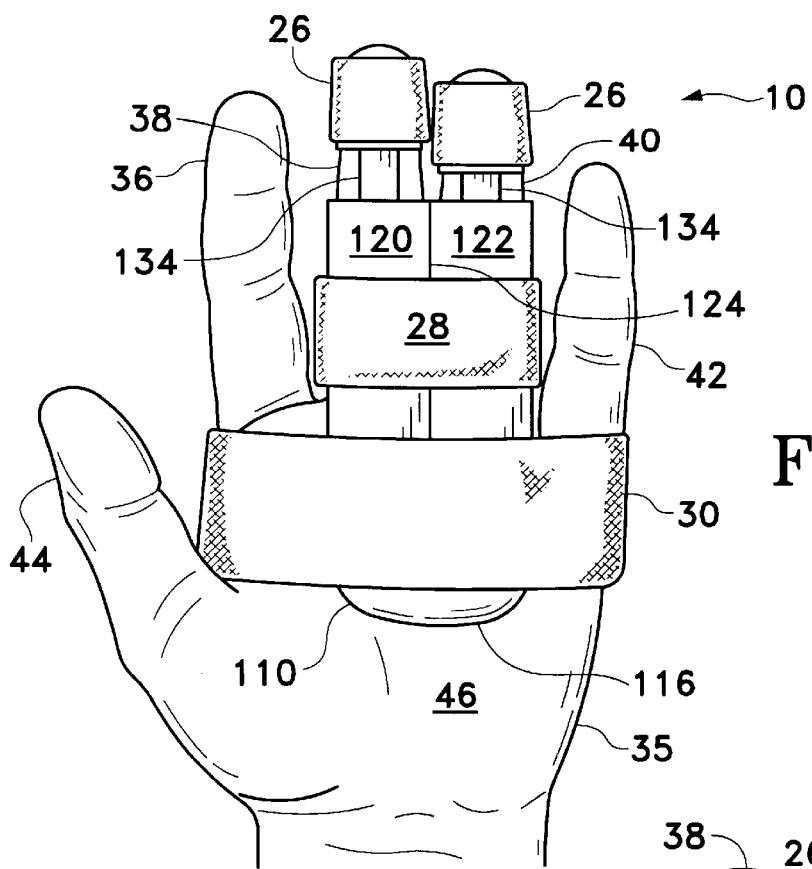
FIG. 16 is a front elevation of the splint of FIG. 14 shown in use on the middle and ring fingers of a patient.
Figure 17:
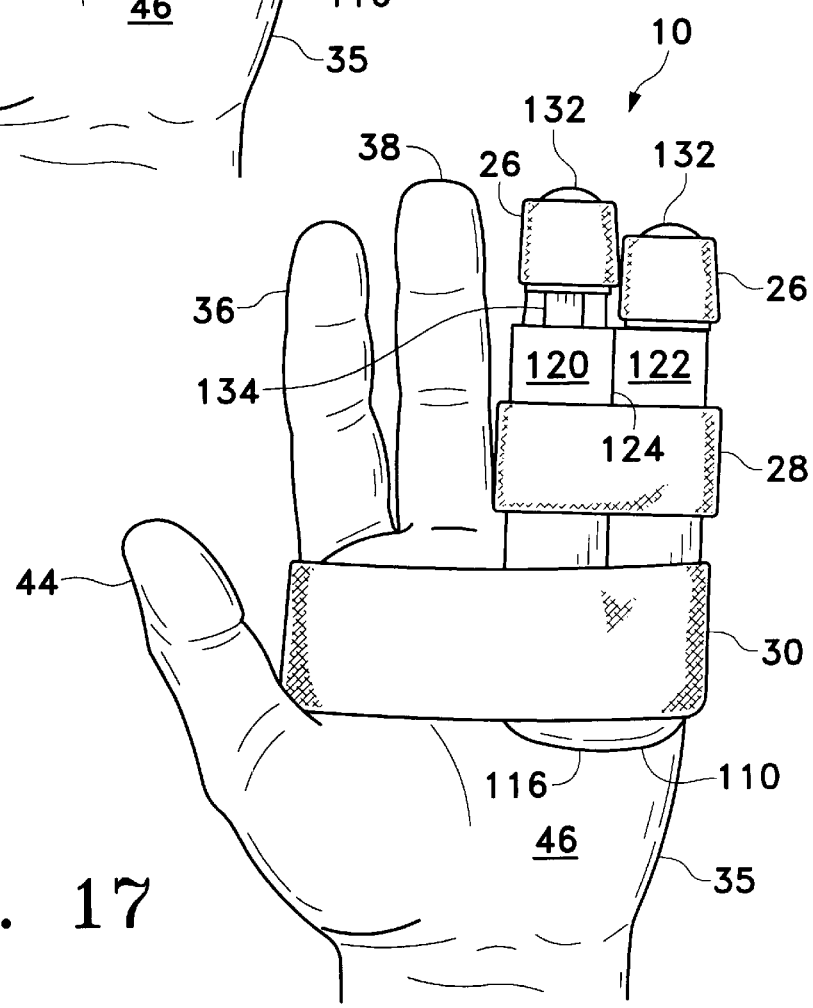
FIG. 17 is a front elevation of the splint of FIG. 14 shown in use on the ring and pinkie fingers of a patient.

Referring now to FIG. 16, the splint system 10 of FIG. 14 is shown in use in splinting the middle finger 38 and ring finger 40. Referring to FIG. 17, the same splint system 10 of FIG. 14 is shown splinting the ring finger 40 and the pinkie finger 42. The same two finger splint system 10 of FIG. 14 can be used to splint any two adjacent fingers. The ability to adjust the length of each splint by means of the extension tip members 123 allows the same splint to be used with patients having different lengths of fingers and with different groups of fingers on one person's hand, as clearly seen in FIGS. 15–17.

Figure 18:
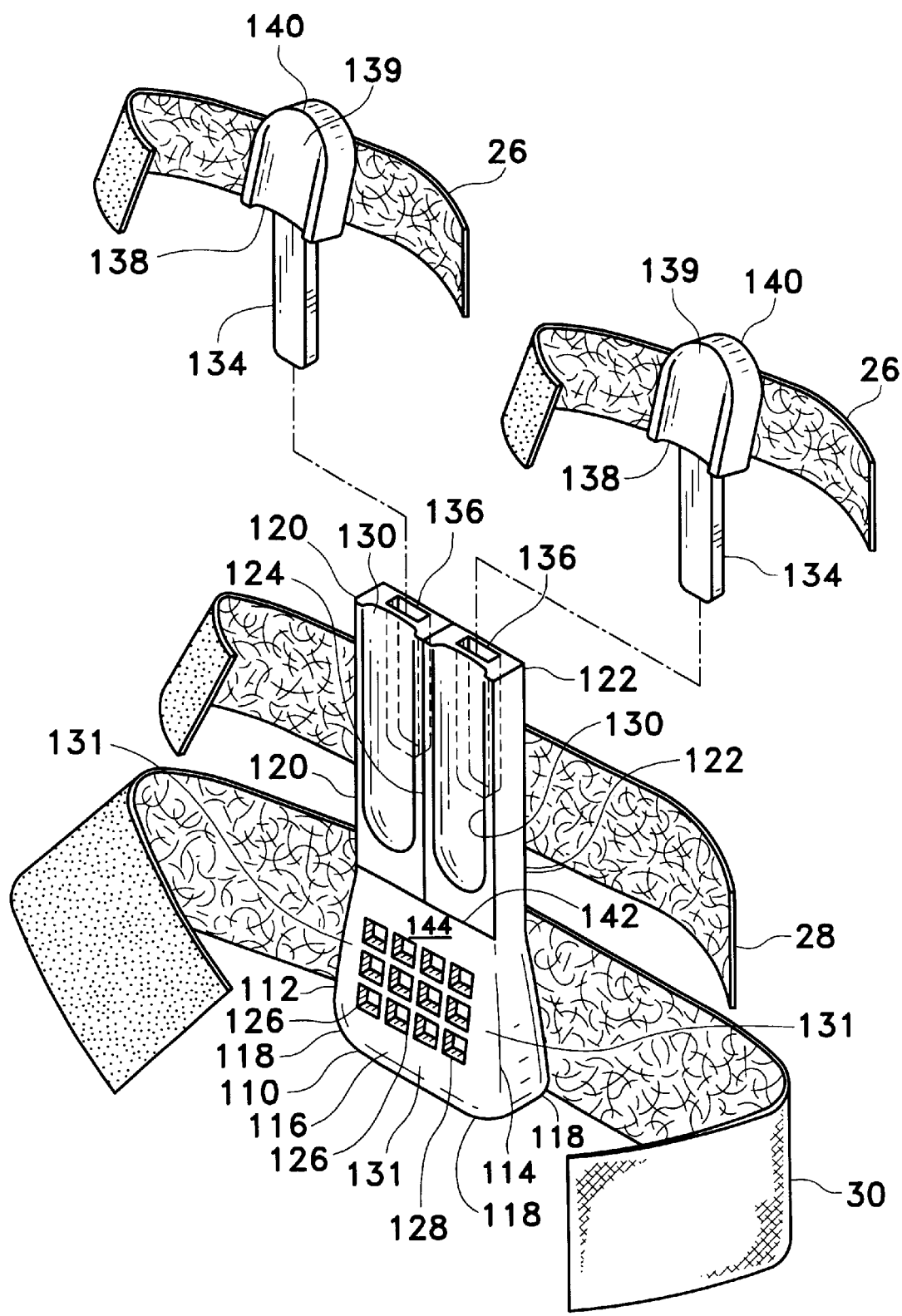
FIG. 18 is a rear elevation of an embodiment of the splint of FIG. 1 for use with any three adjacent fingers.
Figure 19:
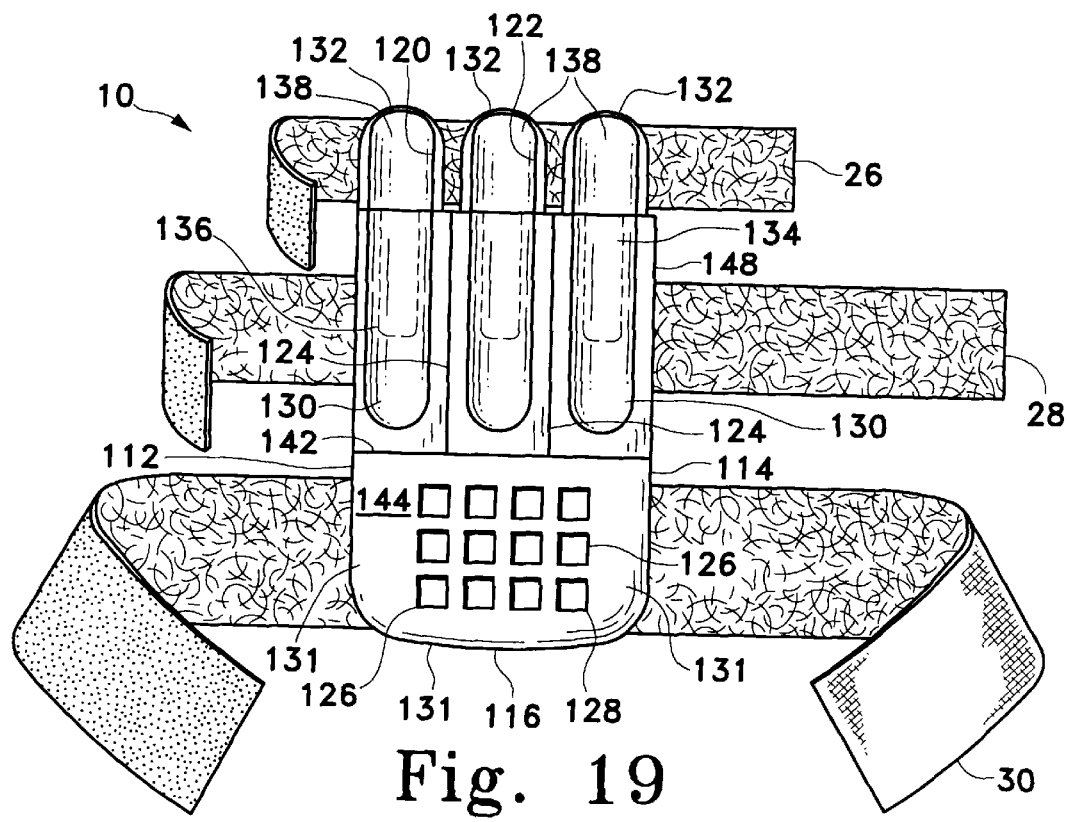
FIG. 19 is a front elevation of the splint of FIG. 18 shown in use on the index, middle and ring fingers of a patient.

Referring now to FIG. 18, the two-finger splint system 10 of FIG. 14 is shown in perspective exploded fashion with bent tip extension members, similar to those described above in connection with FIGS. 4, 5 and which are described in the present embodiment in connection with FIGS. 23–28 below. As seen in FIG. 18, the base 110 flares outwardly from a neck portion to the bottom edge 116, widening at a uniform rate from the neck 142 to the bottom edge 116 along both the rear face 144 (that is, from left to right as shown in FIGS. 14, 18) thereby becoming wider, and from the front 146 to the rear face 144, thereby becoming thicker and producing a bulbous base 110. That is, the bulbous base 110 tapers from the bottom edge 116 to the neck 142.

Referring now to FIGS. 19–22, there is shown a three-finger splint system 10, which is identical to the two-finger splint system 10 of FIGS. 14–18, except that it includes a co-joined third splint body 148 adjacent to and rightward of the right-hand splint body member 122 of FIG. 14 (or the third splint body 148 can be considered as leftward of and adjacent to the left-hand splint body member 120, or as lying between the left-hand 120 and right-hand splint body members 120, 122). All three of the splint body members 120, 122, and 148 are connected to the base 110, which is wider than that shown in FIG. 14 and there is a seam 124 between each adjacent splint body member. A separate short fastening strip 26 is attached to all thee extension tip members 132.

Figure 20:
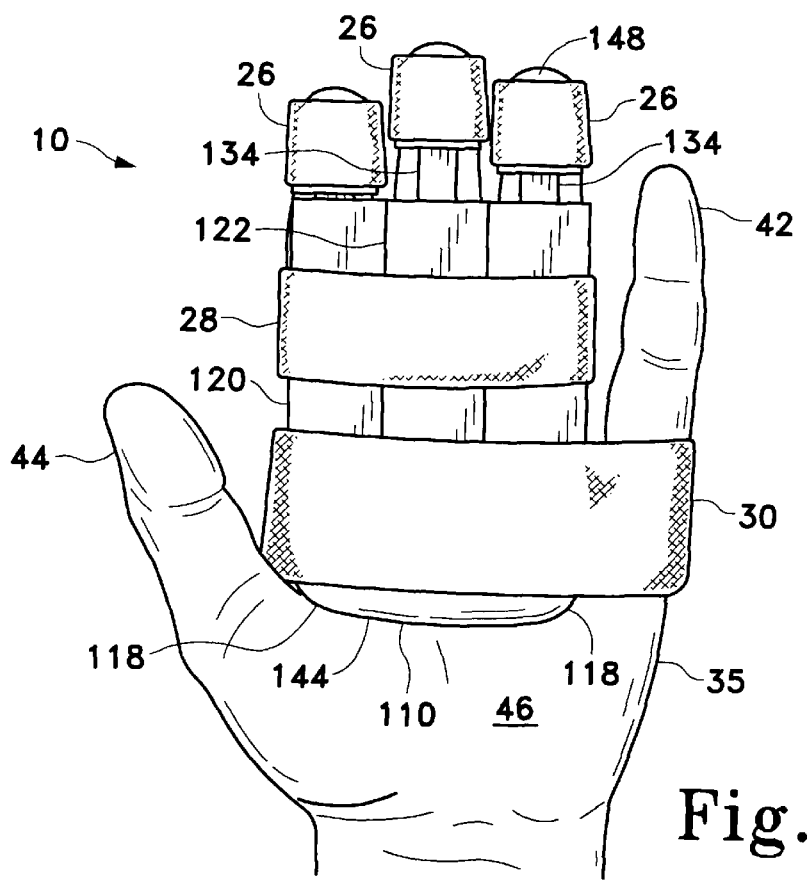
FIG. 20 is a front elevation of the splint of FIG. 18 shown in use on the middle, ring, and pinkie fingers of a patient.

Referring now to FIG. 20, the three-finger splint system 10 is shown splinting the index finger 36, middle finger 38, and the ring finger 40. Referring now to FIG. 21, the same splint system 10 is shown splinting the middle finger 38, the ring finger 40, and the pinkie finger 42. Due to the adjustable length extension tip members 132, the same three-finger splint system 10 can be used on patients with different sized hands or on the different lengths of fingers on one patient's hands. The middle length fastening strip 26 wraps around the splinted fingers and each of the splint body members of a particular splint system 10, for example two fingers are wrapped by the fastening strip 28 in the two-finger splint of FIG. 14 and around three fingers in the three-finger splint system 10 of FIG. 19.

Referring now to FIG. 24, the extension tip members 132 have been replaced with bent extension tip members 150. Straight extension tip members 132 and bent extension tip members 150 are mechanically interchangeable in any finger splint system 10 described herein and may be mixed within any multiple finger splint described herein as needed for a particular treatment regime, although normally all splinted fingers will be splinted either in by a straight splint tip, a bent splint tip bent forward or a rearwardly bent splint tip.

Figure 27:
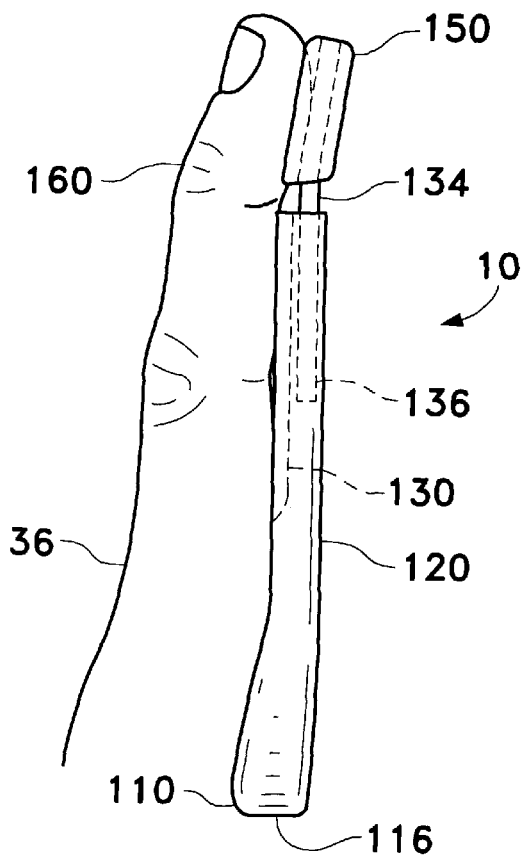
FIG. 27 is a right-hand side elevation of the bent tip extension member of FIG. 21 shown in use on a finger bending the tip of the finger forward.
Figure 28:
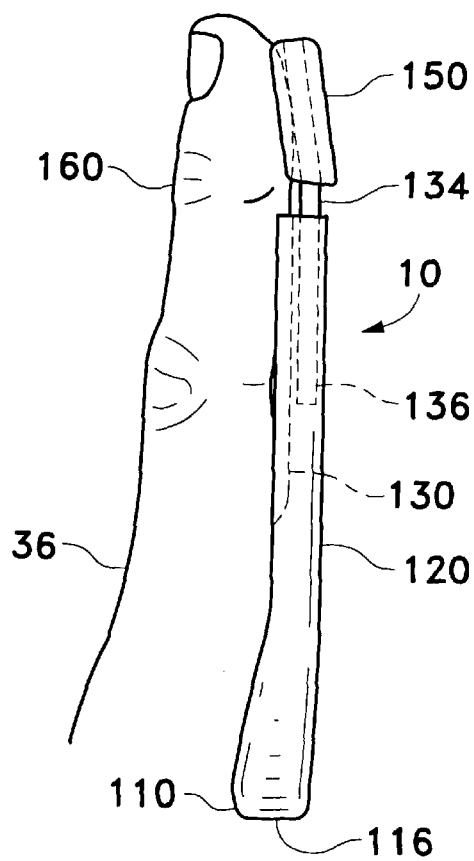
FIG. 28 is a right-hand side elevation of the bent tip extension member of FIG. 21 shown in use on a finger and bending the tip of the finger backward.

Referring now to FIGS. 24, 28, the bent tip extension member 150 is shown bending the tip of the index finger 36 rearwardly or backward, whereas in FIGS. 23, 27, the same bent tip extension member 150 is shown bending the index finger 36 forward. Either two, three, or four fingers are similarly bent at the tip, but are not visible in the views shown.

Figure 25:
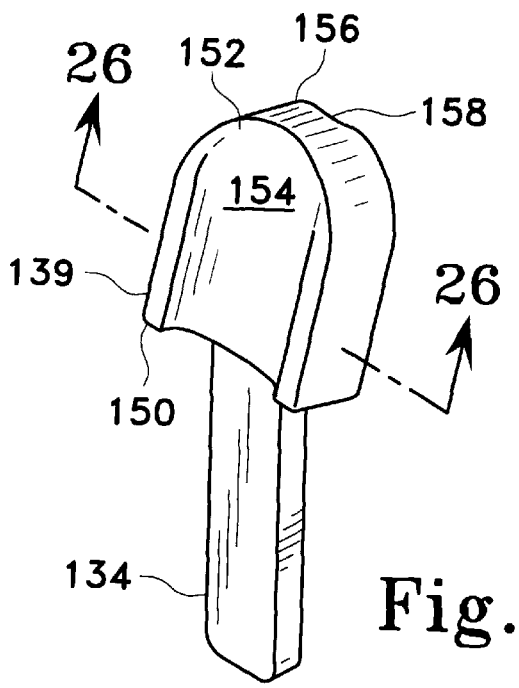
Figure 26:
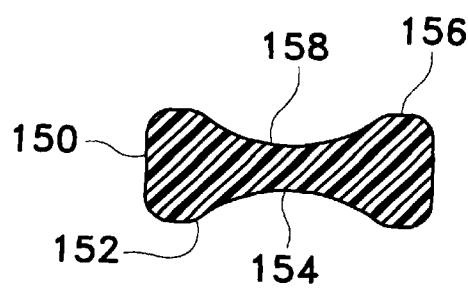
FIG. 26 is a cross section view of the bent tip extension member of FIG. 21 taken along lines 26—26 of FIG. 25.

Referring now to FIGS. 25, 26, it is apparent that the same bent tip extension member 150 can be used either to bend the finger forward or rearward because there is a finger accepting groove on both faces of the extension tip member. That is the front face 152 of the extension tip member 150 includes the front face finger receiving groove 154 and the rear face 156 of the extension tip member 150 includes the rear face finger receiving groove 158, thereby providing a finger receiving groove 154 or 158 to the patient's finger regardless of whether the face 152 or 156 is presented against the patient's finger when installed, thus allowing the same extension tip member 150 to be used to bend the finger or fingers forward or backward. With all bent extension tips 132, 150, the tongue 20, 134 and fingertip pad 139 are connected along a non-linear path, that is the fingertip pad 139 portion lies at an angle to the bent extension tips 132, 150 and these two elements do not lie along a straight line relative to one another.

As shown, the bent tip extension members typically bend the finger 36, 38, 40 or 42, or any number of them, either forward or backward at the upper flange 160, that is only at the top knuckle, but the bent extension tip members may be made longer and the splint bodies shorter to allow for bending at any knuckle of any finger. The angle at which the finger or fingers are bent can also be changed. In one embodiment, the bent tip extension members are include a tongue member 134 made from metal that can be bent to any desired angle by the physician when installing the splint system 10. In another embodiment, the bent tip extension members are wholly made from plastic and the bent extension tip member 150, for example, is molded at a set angle, with different models being bent at different angles. In all cases, the bent tip extension members have tongues 134 that will fit into any tongue receiving slot or channel 136 in any splint system. 10, with the slot 136 being aligned along a longitudinal axis of any splint body member described herein.

The invention made be made of injection molded plastic or other convenient materials. The straps are preferably made from fabric. They may be attached to the respective embodiments by any suitable adhesive, or they may be unattached and held in position during use by the frictional engagement of the fastening system, which may be any convenient system, such as the hook and loop fasteners described herein, or by buckles or the like.

While the present invention has been described in accordance with the preferred embodiments thereof, the description is for illustration only and should not be construed as limiting the scope of the invention. Various changes and modifications may be made by those skilled in the art without departing from the spirit and scope of the invention as defined by the following claims.

I claim:

1. A splint system for two or more fingers of the hand comprising:
   a. a base adapted to fit into the palm of the user's hand, said base further comprising a U-shaped lower edge, said base being connected to at least two splint body members, each said splint body member further comprising an upper end and a lower end, each splint body member further comprising a depending tongue member receiving channel formed in said upper end of each said splint body, said depending tongue member receiving channel aligned with a longitudinal axis of each said splint body and contained wholly within each splint body, each said depending tongue member receiving channel extending downwardly from each said upper end of said splint body; and
   b. an extension tip member having a depending tongue member slidably received in said depending tongue member receiving channel of each said splint body with sufficient frictional engagement between each said depending tongue member receiving channel and each said depending tongue member of said extension tip to maintain said extension tips in a desired position relative to said splint body such that when placed on the hand of a user, each said splint member is adapted to extend only from the metacarpals to the proximal phalange which each said splint member covers.

2. A splint system for two or more digits of the hand in accordance with claim 1 wherein each said splint body member and each said extension tip further comprises a concave inner surface for conforming to the shape of a finger.

3. A splint system for two or more fingers of the hand in accordance with claim 1 further comprising a means for fastening said splint system to said hand and to said fingers.

4. A splint system for two or more fingers of the hand in accordance with claim 3 wherein said plurality of straps further comprises three spaced parallel straps attached to said splint system for securing said splint member to a hand.

5. A splint system for two or more fingers of the hand in accordance with claim 1 further comprising four splint members connected together along a common base adapted to fit in the palm of a user's hand with each said splint member having an extension tip member.

6. A splint system for two or more fingers of the hand in accordance with claim 5 wherein said extension tip member further comprises a fingertip pad having a front face finger receiving groove and a rear face finger receiving groove.

7. A splint system for two or more fingers of the hand in accordance with claim 6 wherein said tongue and said fingertip pad are connected along a non-linear path.

8. A splint system for two or more fingers of the hand comprising:
   a. a base adapted to fit into the palm of the user's hand, said base further comprising a U-shaped lower edge, said base being connected to at least two splint body members, each said splint body member further comprising an upper end and a lower end, each splint body member further comprising a depending tongue member receiving channel formed in said upper end of each said splint body, said depending tongue member receiving channel aligned with a longitudinal axis of each said splint body and contained wholly within each splint body, each said depending tongue member receiving channel extending downwardly from each said upper end of said splint body; and b. an extension tip member having a depending tongue member slidably received in said depending tongue member receiving channel of each said splint body with sufficient frictional engagement between each said depending tongue member receiving channel and each said depending tongue member of said extension tip to maintain said extension tips in a desired position relative to said splint body such that when placed on the hand of a user, each said splint member is adapted to extend only from the metacarpals to the proximal phalange which each said splint member covers, wherein said two splint body members are arranged immediately adjacent to one another and parallel to one another for splinting two adjacent fingers of the user's hand, whereby the index and middle finger, or the middle finger and ring finger or the ring finger and the little finger can be splinted together with the same splint body system.

9. A splint system for two or more fingers of the hand in accordance with claim 8 wherein said two immediately adjacent splint body members are joined together into a single splint body whereby two splinted fingers are held immobile relative to each other.

\* \* \* \* \*